United States Patent [19]

Knifton

[11] Patent Number: 5,313,006
[45] Date of Patent: May 17, 1994

[54] COGENERATION OF ISOBUTYLENE PLUS MTBE FROM CRUDE T-BUTANOL/METHANOL FEEDSTOCKS

[75] Inventor: John F. Knifton, Austin, Tex.

[73] Assignee: Texaco Chemical Company, White Plains, N.Y.

[21] Appl. No.: 994,015

[22] Filed: Dec. 21, 1992

[51] Int. Cl.$^5$ .............................................. C07C 41/09
[52] U.S. Cl. .................................................... 568/698
[58] Field of Search .................................... 568/695

[56] References Cited

U.S. PATENT DOCUMENTS

| | | | |
|---|---|---|---|
| 4,886,918 | 12/1989 | Sorenson | 568/698 |
| 4,906,787 | 3/1990 | Huang et al. | 568/698 |
| 4,943,545 | 7/1990 | Chang et al. | 502/27 |
| 5,162,592 | 11/1992 | Knifton et al. | 568/698 |

OTHER PUBLICATIONS

Rozhkov et al., Prevzasch Uylevodorsdov Kislotno-Oshovn, Geterogennyth Katal, Tezisy Dokli Vses Kouf 1977 pp. 150–152.

Primary Examiner—Howard T. Mars
Attorney, Agent, or Firm—James L. Bailey; Kenneth R. Priem; Cynthia L. Kendrick

[57] ABSTRACT

Disclosed is an improvement in a method for cogeneration of isobutylene and MTBE by etherification of tBA/MeOH over an ion-exchange resin which allows for more complete conversion of the remaining tBA fraction and comprises a second step consisting essentially of recovering the MTBE from the primary fractionator as an overhead fraction and etherifying the bottoms from the primary fractionator over an inorganic acid catalyst comprising a crystalline aluminosilicate faujasite-type Y-zeolite modified with a compound selected from a fluoride-containing compound including hydrofluoric acid, ammonium fluoride, fluorosulfonic acids and their cogeners and triflic anhydride at a temperature of greater than 120° C.

9 Claims, No Drawings

COGENERATION OF ISOBUTYLENE PLUS MTBE FROM CRUDE T-BUTANOL/METHANOL FEEDSTOCKS

CROSS-REFERENCE

This application is related to U.S. Pat. Nos. 5,099,072, 5,169,592 and 5,081,318, and to application Ser. No. 07/917,885.

This invention concerns the cogeneration of isobutylene and MTBE from crude t-butanol/methanol feedstocks. More particularly it concerns improved conversions of t-butanol to methyl tertiary butyl ether in a method comprising removing the bottoms from a primary fractionator of a unit for making MTBE and further reacting them over an acidic, fluoride-treated Y-zeolite at temperatures greater than 120° C. Coreactants in the crude feedstock may comprise water, t-butanol, methanol and isopropanol. Reaction over preferred fluoride treated Y-zeolites brings the total t-butanol conversion up to >90% in a continuous unit.

In addition, product phase separation is observed at 160° C.–220° C. into an isobutylene/MTBE product-rich phase and an aqueous methanol heavier phase.

BACKGROUND OF THE INVENTION

It is known to those skilled in the art that ethers, including unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Methyl tert-butyl ether is finding increasing use as a blending component in high octane gasoline as the current gasoline additives based on lead and manganese are phased out. Currently most commercial processes for the manufacture of methyl tert-butyl ether are based upon the liquid-phase reaction of isobutylene and methanol (Eq. 1), catalyzed by a cationic ion-exchange resin (see, for example: Hydrocarbon Processing, October 1984, p. 63; Oil and Gas J., Jan. 1, 1979, p. 76; Chem. Economics Handbook-SRI, September 1986, p. 543–7051P). The cationic ion-exchange resins used in MTBE synthesis normally have the sulphonic acid functionality (see: J. Tejero, J. Mol. Catal., 42 (1987) 257; C. Subramamam et al., Can. J. Chem. Eng., 65 (1987) 613).

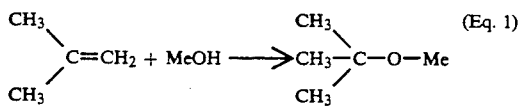

(Eq. 1)

With the expanding use of MTBE as an acceptable gasoline additive, a growing problem is the availability of raw materials. Historically, the critical raw material has been isobutylene (Oil and Gas J., Jun. 8, 1987, p. 55), however, recently, U.S. Pat. Nos. 5,099,072, 5,169,592 and 5,081,318, inter alia, assigned to Texaco Chemical, disclose a one-step method for producing methyl tert-butyl ether (MTBE) from t-butanol (tBA) over various catalysts. It would be advantageous to obtain additional conversion of the t-butanol in the crude feedstock without having to recycle unconverted tertiary butanol.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl. Vses Konf., 1977, 150 (C. A. 92:58165y). Here the tBA and methanol undergo etherification over KU-2 strongly acidic sulfopolystyrene cation-exchangers under mild conditions. This reference contains data on basic parameters of such a process. It is also noted that, although a plant for etherification over cation exchangers does not present any major problems, considerations include the fact that recycling large amounts of tert-butyl alcohol and methanol, as well as isobutylene, causes the scheme to be somewhat more expensive. Also, the progress of the reaction over cation exchangers is usually complicated by various adsorption and diffusion factors, by swelling phenomena, and by the variable distribution of the components between the solution and ion-exchanger phase. Furthermore, said acidic cation-exchangers with an organic (polystyrene or polymethacrylate) backbone generally have a very limited stability range with regard to operating temperatures, with temperatures above 120° C. normally leading to irreversible destruction of the resin and loss of catalytic activity.

"Preparation of Methyl Tert-Butyl Ether (MTBE) Over Zeolite Catalysts" is an article by Pochen Chu and Günther H. Kühl, Ind. Eng. Chem. Res., 26, 365, 1987. Chu et al. disclose work which identifies ZSM-5 and ZSM-11 to be selective for the preparation of MTBE. Compared to the conventional Amberlyst 15 resin, the zeolites are thermally stable, and give no acid effluent; they provide high selectivity to MTBE with little or no diisobutene yield, are less sensitive to the $CH_3OH/i\text{-}C_4H_8$ ratio and exhibit good selectivity even at ratios approaching unity. They provide high MTBE output, despite the unfavorable thermodynamic equilibrium, since the process utilizing these zeolites can be operated at high temperature and high space velocity. In addition, deactivation is not observed in the present short catalytic tests and reactivation is not required. The excellent selectivity of these two zeolites is believed to be effected by the size of their pore structure, which provides easy access to methanol and restricted access to isobutene. Zeolite beta was also tested, giving the poorest results and small pore zeolites were inactive. As expected, large pore zeolites do not exhibit shape selectivity.

An extensive body of knowledge of zeolite properties and catalytic potential has developed in recent years. A variety of different types of zeolites is known in the art, including natural and synthetic zeolites. Research has opened up a spectrum of new opportunities in the field of molecular shape selective catalysis, where the intracrystalline space accessible to molecules has dimensions near those of the molecules themselves. This field is discussed in an article titled "Molecular Shape Selective Catalysis", P. B. Weisz, New Horizons in Catalysis, Part A, 1980. For example, it is possible to catalyze the dehydration of n-butanol over a Linde 5Å zeolite without reacting isobutanol which may be present. Such research has led to the concept of molecular engineering.

Early work in molecular engineering was very limited by the choice of zeolites. This limitation lead to the discovery of methods for zeolite synthesis, using large organic cations as templates in place of the traditional all-inorganic ionic species. This research opened the way to the synthesis of many new zeolites. Now a number of industrial processes, including selectoforming, M-forming, dewaxing, xylene isomerization, ethyl benzene production, toluene disproportionation and methanol-to-gasoline are based on shape selective zeolites. Since the early demonstrations of product selectivity, many more cases have been observed and many reviewed and reported by Csicsery and Derouane. See S. M. Csicsery,"Zeolite Chemistry and Catalysis", ACS Monograph 171, J. A. Rabo, Ed., American Chemical Society, Washington, D.C. (1976), and E. G. Derouane. "Diffusional Limitations and Shape Selective Catalysis in Zeolites", from Intercalation Chemistry, M. S. Whittinham, A. J. Jacobson, Eds., Academic Press, New York.

The natural crystalline aluminosilicate zeolites can be represented by the empirical formula:

$$M_{2/n}O \cdot Al_2O_3 \cdot xSiO_2 \cdot yH_2O$$

The synthetic X and Y type zeolites have framework structures similar to that of the natural mineral faujasite although they are distinct species. The unit cells are cubic with a cell dimension of nearly 25Å. Each unit cell contains 192 $SiO_4$ and $AlO_4$ tetrahedra that are linked through shared oxygen atoms. See "Molecular Sieve Catalysis", J. W. Ward, Applied Ind. Catal., Vol. 3, 1984.

In the Y zeolites the three-dimensional framework comprising a tetrahedral arrangement of connected truncated octahedral provides giant supercages approximately 13Å in diameter with eight supercages per unit cell. The supercages are interconnected by twelve-membered rings of about 8Å in diameter. Many different chemical species can be absorbed by this large-pore system. Ibid., p. 275.

Various zeolites have characteristic structures which favor certain types of reactions. For instance, mordenite is one of the most silica-rich zeolite minerals, having a $SiO_2/Al_2O_3$ ratio of about 10. The structure consists of chains of tetrahedra cross-linked by the sharing of oxygen atoms. Mordenite has high thermal stability, probably due to the presence of the large number of five-membered rings that are energetically favored. The dehydrated structure has a two-dimensional channel system accessible to small molecules, but not to typical hydrocarbon molecules. Ibid., pp. 275-6.

Erionite is probably the smallest pore zeolite used commercially.

A number of zeolites have been synthesized that have $SiO_2/Al_2O_3$ ratios greater than 10 or are essentially pure silicas. Examples of those which have found commercial utility because of their shape selective properties are ZSM-5 and ZSM-11. Some of these zeolites are aluminum-free silicalites which have no ion-exchange properties and should properly be regarded as molecular sieves.

The Ward reference, ibid, offers a review of molecular sieve zeolites used in catalysis. Though zeolites have been known for a long time, the major stimulus in molecular sieve science came with the first synthesis of A zeolite by Milton, described in U.S. Pat. No. 2,882,243 (1959).

Zeolite molecular sieves can be modified by treatment by cation exchange, thermal or hydrothermal treatment and chemical modification. Most catalytic preparations involve an ammonium ion exchange, typically by refluxing the zeolite with at least a five-fold excess of aqueous ammonium salt.

Divalent cation exchange with elements such as calcium and magnesium is considered rather difficult according to Ward.

Rare earth ion exchange zeolites have played an important role in zeolite catalysis, particularly in fluid cracking catalysts and require multiple batch exchanges at elevated temperatures with excess solutions. Ibid., pp. 288-289.

Zeolites having higher silica/alumina ratios are more stable and, therefore, more suitable for treatment. Careful acid treatment can result in up to 75% of the alkali metal ions being replaced before structural collapse occurs. Ibid., p. 290.

The thermal or hydrothermal treatment of zeolites is also known. Thermal treatment of synthesized X and Y zeolites has no structural effects on the zeolite until the decomposition temperature of about 800° C. is reached. It is possible to exchange and reexchange ions. For instance, it is possible to exchange with ammonium ions, calcine and exchange with rare earth. Ibid., p. 292.

Zeolites lose physically bound water on heating to about 150° C. and exotherms around 800° C. represent structural collapse of the zeolite. The hydroxyl groups are believed to be in different parts of the structure, some in supercages and some inaccessible to most absorbing molecules.

Zeolites can be modified to remove alumina by treatment with chelates such as acetylacetone and ethylenediamine tetraacetic acid. Aluminum atoms can be replaced with silicon tetrachloride or treatment with ammonium fluorosilicate. Ibid., p. 298.

A number of commercial applications of these synthetic zeolites are discussed in "Synthetic Zeolites in Commercial Applications", R. G. Muller, et al., SRI PEP Review v. 81-3-3 (1982). Due to the unique structure of zeolites and to the knowledge available today regarding properties and manufacturing processes, many uses have been discovered for zeolites in adsorbent and catalytic applications. Some of the reactions for which synthetic zeolites have been shown to be active catalysts include xylene isomerization, naphtha isomerization, light olefin oligomerization, toluene dealkylation, benzene hydrogenation, olefin and fat hydrogenation, methanation, dehydrogenation of ethylbenzene, dehydrohalogenation, desulfurization and propylene carbonylation.

Another good reference for familiarization with the relationship between molecular shapes, structures of zeolites and selectivity for certain catalysis is an article titled "Industrial Application of Shape Selective Catalysis", N.Y. Chen et al., Catal. Rev.-Sci. Eng., 28 185 (1986).

The zeolites of interest to shape-selective catalysis may be divided into three major groups according to their pore/channel systems. The first group includes 8-membered oxygen ring systems such as, for example, Linde A, erionite, chabazite, zeolite alpha, ZK-4, ZK-21, ZK-22 and several other less common natural zeolites.

The second group includes 10-membered oxygen ring systems such as, for example, ZSM-5, ZSM-11, ZSM-22, ZSM-23, ZSM-48 and laumontite, which has a puckered 10-membered oxygen ring. The rest of the medium pore zeolites are usually synthetic in origin; they are sometimes known as pentasils. They have a predominance of silicon.

The third group of zeolites is those having dual pore systems which have interconnecting channels of 12- and 8-membered oxygen ring openings. Examples include mordenite, offretite, clinoptilolite, ferrierite, etc.

There is a survey of aluminosilicate catalyst reactivity and of reactions catalyzed by aluminosilicates in an article titled "Clays, Zeolites and other Microporous Solids for Organic Synthesis," by John M. Thomas et al., in Modern Synthetic Methods, 1989, Vol. 5, p. 249.

It is stated at page 263 that the valency or the size of the exchangeable cation can be adjusted, thus fine-tuning the molecular sieving and shape-selective properties. For example, in the Na+ form of zeolite-alpha, the effective void space within the zeolite can be enlarged by replacement of Na+ by $Ca^{2+}$ ions.

Dealumination of a zeolite can enhance the microporosity of a zeolite by increasing the Si/Al ratio of the anionic framework and can be represented by the following:

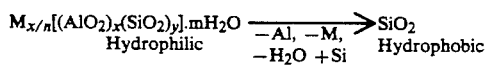

$$M_{x/n}[(AlO_2)_x(SiO_2)_y]\cdot mH_2O \xrightarrow[-H_2O\ +Si]{-Al,\ -M,} SiO_2$$
Hydrophilic → Hydrophobic Hydrothermal treatment Will result in ultra-stabilization of the zeolite and recent work indicates Si:Al ratios can be increased to greater than 1000.

More than 40 distinct species of zeolite materials have been identified and there are at least 130 synthetic species. The pore sizes and compositions of typical commercially available zeolites are shown in Table A.

TABLE A
COMMERCIALLY AVAILABLE ZEOLITES

| Zeolite | Pore Size/nm | Composition Si/Al | Cation | Sorption Capacity (wt %) $H_2O$ | $nC_6H_{14}$ | $C_6H_{12}$ |
|---|---|---|---|---|---|---|
| Faujasite | | | | | | |
| X | 0.74 | 1–1.5 | Na | 28 | 14.5 | 16.6 |
| Y | 0.74 | 1.5–3 | Na | 26 | 18.1 | 19.5 |
| US-Y | 0.74 | >3 | H | 11 | 15.8 | 18.3 |
| A | 0.3 | 1.0 | K, Na | 22 | 0 | 0 |
| A | 0.4 | 1.0 | Na | 23 | 0 | 0 |
| A | 0.45 | 1.0 | Ca, Na | 23 | 12.5 | 0 |
| Chabazite | 0.4 | 4 | * | 15 | 6.7 | 1 |
| Clinoptilite | 0.4 × 0.5 | 5.5 | * | 10 | 1.8 | 0 |
| Erionite | 0.38 | 4 | * | 9 | 2.4 | 0 |
| Ferrierite | 0.55 × 0.48 | 5–10 | H | 10 | 2.1 | 1.3 |
| L-type | 0.6 | 3–3.5 | K | 12 | 8 | 7.4 |
| Mazzite | 0.58 | 3.4 | Na, H | 11 | 4.3 | 4.1 |
| Mordenite | 0.6 × 0.7 | 5.5 | * | 6 | 2.1 | 2.1 |
| Mordenite | 0.6 × 0.7 | 5–6 | Na | 14 | 4.0 | 4.5 |
| Mordenite | 0.6 × 0.7 | 5–10 | H | 12 | 4.2 | 7.5 |
| Offretite | 0.58 | 4 | K, H | 13 | 5.7 | 2.0 |
| Phillipsite | 0.3 | 2 | * | 15 | 1.3 | 0 |
| Silicalite | 0.55 | ** | H | 1 | 10.1 | 0 |
| ZSM-5 | 0.55 | 10–500 | H | 4 | 12.4 | 5.9 |

*Denotes a mineral zeolite: cations variable, but usually Na, K, Ca, Mg
**Very large Si:Al Another important aspect regarding zeolites involves methods of generating acidity. Several ways of introducing acidity into a zeolite are known in the art and they result in the formation of Bronsted acid sites. The total acidity of a zeolite catalyst depends on both the concentration of acidic sites and the strength of the individual sites. The number and nature of active sites in a zeolite catalyst can be determined in several ways, including $^{27}Al$ solid state NMR, uptake of base and poisoning experiments. Maximum overall acidity is often found for Si/Al ratios in the range of 5 to 20. Bronsted acid sites formed by various methods can form Lewis acid sites by dehydroxylation:

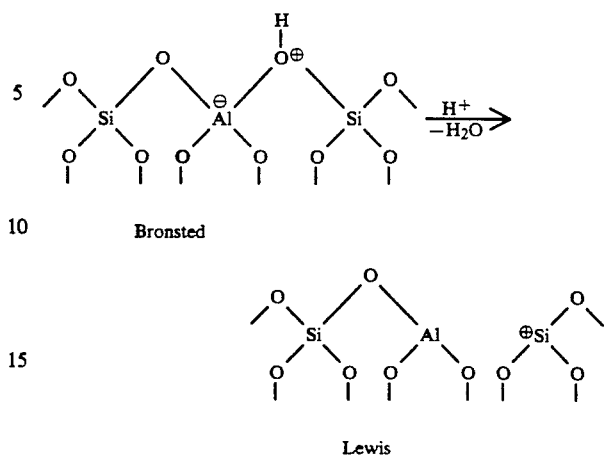

Bronsted

Lewis

Where shape selectivity by size exclusion is the key to zeolite function, it can be accomplished either through reactant selectivity or product selectivity. It is believed Columbic field effects may also play a part. Another phenomenon which has been observed to contribute is configurational diffusion which occurs in situations where structural dimensions of the catalyst approach those of molecules; even subtle changes in dimensions of molecules can result in large changes in diffusivity, see Chen et al., Catal. Rev.-Sci. Eng., supra, p. 198.

Another type of selectivity which has been observed is spatiospecificity or restricted transition state, where both the reactant molecule and the product molecule are small enough to diffuse through channels, but the reaction intermediates are larger than either the reactants or the products and are spatially constrained. This is one of the most important properties of ZSM-5. Some zeolites, such as ZSM-5, ferrierite, cliniptilolite, offretite and mordenite have intersecting channels of differing channel size and may exhibit the phenomena of traffic control, see Ibid., p. 198.

Reactants which are of particular interest in shape selective catalysis include straight-chain and slightly branched paraffins and olefins, naphthenes and aromatics.

A concise and informative review of zeolite applications in organic synthesis is titled "Zeolite Catalysts Face Strong Industrial Future" in European Chemical News, Jul. 10, 1989, p. 23. Points worth noting are that the major success of zeolite catalysis is in catalytic cracking with about 300,000 tons per year being used worldwide. Typically these are zeolite-Y, (12-ring window) but oftentimes a medium-pore, such as H-ZSM-5, is added to increase aromatic content. The ZSM-5 consists of two pore systems (5–6Å in diameter) which intersect to give spatial regions of around 9Å diameter at the intersections.

Early work emphasized the role of medium-pore zeolites for aromatics substitution, but more recently, there has been extensive work describing the role of zeolites in the synthesis of organic intermediates containing oxygen and nitrogen, Ibid, p. 24.

In U.S. Pat. No. 4,214,307 to C. D. Chang et al. (Jul. 22, 1980), it is shown that hydration of $C_2$ to $C_4$ olefins to alcohols can be carried out over ZSM-5 below about 240° C. and 10 to 20 atmospheres of pressure without forming ethers or other hydrocarbons, however, above 240° C. propene and butenes undergo other olefinic reactions, forming higher molecular weight hydrocarbon products.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

In U.S. Pat. No. 4,943,545, to Chang et al., there is suggested modification of Y-zeolites having Si:Al ratio of at least 4 with a very dilute (0.001→0.1N) solution of HF in a cracking catalyst as a means of reactivation.

U.S. Pat. No. 4,605,787 discloses a process for the preparation of methyl tert-butyl ether which comprises reacting methanol and isobutylene in vapor phase in the presence of ZSM-5 or ZSM-11 acidic zeolite catalyst.

U.S. Pat. Nos. 5,099,072; 5,169,592 and 5,081,318, assigned to Texaco Chemical Co., relate to various zeolite catalysts used in the one-step synthesis of methyl t-butyl ether from t-butanol.

In U.S. patent application Ser. No. 07/745,777 there is disclosed a catalyst for synthesis of MTBE from t-BuOH comprising hydrogen fluoride modified zeolites.

In U.S. patent application No. 07/917,885, there is disclosed a catalyst for MTBE synthesis comprising fluorophosphoric acid-modified zeolites.

In the art, where the feedstock for producing MTBE is t-butanol, the conversions are not as high as would be desirable. There does not seem to be any disclosure of a second-stage etherification, wherein bottoms from the primary reactor are reacted in a secondary etherification unit to obtain higher overall conversions. This would allow more complete conversion of t-butanol without the necessity of recycling. The second stage of such a two-step process would require a catalyst which can withstand very high temperatures.

It would be a substantial advance in the art if crude t-butanol/methanol feedstocks could be used and still obtain higher tBA conversions (>90%) and total MTBE+isobutylene selectivity as high as 99%.

SUMMARY OF THE INVENTION

In accordance with certain of its aspects, the novel method of this invention for additional cogeneration of methyl tert-butyl ether from crude tertiary butyl alcohol (t-butanol)/methanol feedstock in a second step, comprises etherification of tertiary butyl alcohol/methanol feed to MTBE, recovery of MTBE in the primary fractionator as an overhead fraction and etherification of the bottoms from the primary fractionator in the presence of a catalyst comprising a Y-zeolite treated with a fluoride-containing compound at an elevated temperature and moderate pressure. Examples demonstrate particularly the effectiveness of a catalyst consisting essentially of a Y-zeolite modified with a compound selected from a fluoride-containing compound, fluorosulfonic acid or its cogeners or triflic anhydride.

The catalyst of the instant invention has proven to be active after 2000 hours of ongoing study.

DESCRIPTION OF THE INVENTION

In the instant process there is a primary etherification step using crude tBA/MeOH to generate methyl tertiary butyl ether (MTBE) over an acidic catalyst. In order to achieve more complete conversion of t-butanol without recycle, the instant invention provides for a second step for etherifying remaining t-butanol over an acidic, fluoride-treated Y-zeolite catalyst.

The effluent from the primary reactor is fed to the methyl tertiary butyl ether recovery distillation tower which recovers MTBE, isobutylene and some methanol overhead while water, tBA and methanol are removed in the bottoms. The bottoms from the primary fractionator, comprising water, t-butanol, methanol and isopropanol are fed into a second etherification unit and reacted over an acidic fluoride-treated Y-zeolite for cogeneration of isobutylene and MTBE. The preferred fluoride-treated Y-zeolites achieve >90% conversion and they are stable at high temperatures.

More particularly the instant process involves:

1) The etherification of tBA/MeOH feed to MTBE over an ion-exchange resin at temperatures of <120° C.;

2) Recovery of the MTBE in the primary fractionator as an overhead fraction;

3) Etherification of the bottoms from the primary fractionator comprising crude t-butanol/methanol feedstock over an inorganic acid catalyst at a temperature in excess of 120° C., e.g. 140°-240° C. to complete the conversion of the remaining tBA fraction to MTBE plus isobutylene. The t-butanol/methanol feedstock comprises four principal components, viz-water, t-butanol, methanol and isopropanol.

The etherification reaction can be represented by:

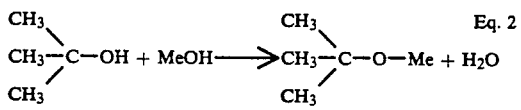

The dehydration reaction can be represented by:

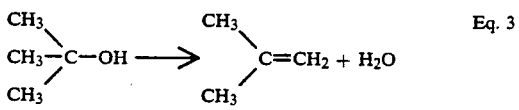

Generally the crude t-butanol/methanol and isopropanol coreactants may be mixed in any proportion in order to generate the desired methyl t-butyl ether. In the initial etherification, the molar ratio of crude methanol feedstock to t-butanol feedstock in the mixture should be between 10:1 and 1:10 if the yield of desired MTBE is to be maximized. The most preferred methanol-to-tertiary butanol molar ratio is from 1:1 to 5:1. In the instant etherification the proportions of coreactants are about 2:1. However, in order to achieve maximum selectivity to MTBE, and optimum conversion per pass, an excess of methanol in the liquid feed is desirable.

The syntheses of Equations 2 and 3 can also be conducted where the t-butanol and methanol reactants are mixed with certain other components including water, alcohols such as isopropanol, ketones such as acetone, peroxides and hydroperoxides such as di-t-butyl peroxide and allyl t-butyl peroxide, as well as esters such as t-butyl formate. Typically each of said classes of components makes up less than 30% of the total feed mixture.

The same process may also be applied to the preparation of other alkyl tertiary alkyl ethers. For example, said process may be applied to the reaction of a $C_1$-$C_6$ primary alcohol such as methanol, ethanol, n-propanol and n-hexanol with a $C_4$-$C_{10}$ tertiary alcohol such as, for example, tertiary butanol and tertiary amyl alcohol.

Reaction of methanol with tertiary amyl alcohol (2-methyl-2-butanol) would then yield methyl tertiary amyl ether (TAME) while reaction of ethanol with t-butanol would yield ethyl t-butyl ether (ETBE). Alternatively a mixture of alcohols, e.g., a mixture of $C_1$–$C_5$ alcohols, could be reacted to give a mixture of alkyl tert-alkyl ethers.

Good results were realized using certain acidic, fluoride-treated Y-zeolites as catalysts for the reactions represented in Equations 2 and 3, particularly the isostructural group of faujasite zeolites that include the synthetic Y-zeolites. The preferred Y-zeolites are the ammonium exchanged and rare earth exchanged Y-zeolites.

The unit cells of zeolites X and Y are cubic, $a_o \approx 2.5$ nm, and each contains 192 silicon- or aluminum-centered oxygen tetrahedra which are linked through shared oxygen atoms. Because of the net negative charge on each of the aluminum-centered tetrahedra, each unit cell contains an equivalent number of charge-balancing cations. These are exclusively sodium ions in zeolites in their synthesized form. Typical cell contents for the Y-zeolites in the hydrated form are:

$$Na_{56}[(AlO_2)_{56}(SiO_2)_{136}] \cdot 250\ H_2O$$

Y-zeolites are distinguished on the basis of the relative concentration of silicon and aluminum atoms and the consequent effects on detailed structure and related chemical and physical properties. The aluminum atoms in the unit cell of Y-zeolite vary from 76 to 48 giving a Si:Al ratio between 1.5 and 3.0. Both the cation concentration and charge density on the aluminosilicate structure are lower for Y-zeolites than for X-zeolites, where the aluminum atoms in the unit cell vary from 96 to 77.

The feature which determines the difference between faujasites and other zeolites built up from sodalite units is the double 6-membered ring or hexagonal prism, by which the units are linked. The sodalite unit, or $\beta$-cage, can be represented by a truncated octahedron, with the 24 silicon or aluminum atoms (designated T atoms) taking positions at the vertices. The 36 oxygen atoms are displaced from the midpoints of the edges joining the vertices in order to attain tetrahedral configuration around the T atoms. The free diameter of the void within the $\beta$-cage is 0.66 nm, but only the smallest molecules can enter through the 0.22 nm diameter opening in the distorted ring of six oxygen atoms associated with each hexagonal face. Each sodalite unit is linked tetrahedrally across hexagonal faces by six bridging oxygens to four other sodalite units. The larger void spaces enclosed by sodalite units and hexagonal prisms are termed $\alpha$-cages, or supercages. The $\alpha$-cage is a 26-hedron with a free diameter of $\approx 1.3$ nm, and it can be entered through four distorted 12-member rings of diameter 0.80–0.90 nm. In this way each $\alpha$-cage is tetrahedrally joined to four others giving a complex system of void space extending throughout the zeolite structure. The $\alpha$- and $\beta$-cages together give Y-zeolites, along with X-zeolites, the largest void volume of any known zeolites, which is ca. 50 vol % of the dehydrated crystal. From the catalytic viewpoint, the $\alpha$-cages are by far the most important, since, unlike the $\beta$-cages, they permit entry of numerous aliphatic and aromatic compounds.

Particularly effective in the subject synthesis of MTBE are the synthetic Y-zeolites. Preferably said zeolites should be in a strongly acidic form whereby some, or all, of the cations (Group I or II, alkali or alkaline earth metal ions such as sodium, potassium, calcium or magnesium) are exchanged by protons either through ammonium exchange followed by thermal stabilization (deammoniation, removal of $NH_3$) at elevated temperatures (e.g. 400°–500° C.) through mineral acid treatment, etc. Alternatively, said Y-zeolites may be rare-earth exchanged with, for example, a mixture of rare-earth salts, by treatment with lanthanum salts, etc. Said rare-earth exchanged Y-zeolites would then have a Si:Al ratio of 1.5 to 3. The exchange of the sodium ions of the Y-zeolite by rare earth ions has been reviewed (see, for example, R. Rudham and A. Stockwell, The Chemical Society Specialist Periodical Report—Catalysis, Vol. I, 1977, Chapter 3). The preferred acidic Y-zeolites for the practice of this invention have silica:alumina ratios in the range 100:1 to 1:1.

Illustrative of suitable Y-zeolites for the practice of this invention include Linde SK-500, a rare-earth exchanged Y-zeolite, having a Si:Al ratio of 1.5→2, PQ Corporation's CP 304-37, a thermally-stabilized, ammonium-exchanged Y-zeolite having a silica:alumina ratio of ca. 11:1, with a silica-alumina binder, as well as CP 316-26, another ammonium exchanged Y-zeolite, this time having a silica-to-alumina ratio of 46, LZY-82 from UOP having a silica:alumina ratio of 7.8 and a unit cell size of 24.53Å, and LZY-85 having a silica:alumina ratio of 9.1 and a unit cell size of 24.49Å.

It has been discovered that acidic fluoride-treated Y-zeolites have a number of improved properties for the production of MTBE. Most importantly they possess the stability at high temperatures necessary for a second stage process of the type described herein. The acid useful for modifying the zeolites is selected from the group consisting of fluoride-containing compounds such as ammonium fluoride or silicon hexafluoride compounds, hydrogen fluoride, hydrofluoric acid, or fluorosulfonic acid and its congeners such as fluorosulfonic acid, trifluoromethane sulfonic acid (triflic acid), as well as triflic anhydride. These fluorosulfonic acids can be substituted with a variety of alkyl groups, as in the case of trifluoromethanesulfonic acid. Methods of preparing these triflic acid-modified catalysts are illustrated in the accompanying Example 2.

The fluoride-modified zeolites are prepared by treating the Y-zeolite or dealuminized Y-zeolite with hydrogen fluoride, with an aqueous solution of hydrofluoric acid, with ammonium fluoride, or with a solution of HF or $NH_4F$ in a suitable organic solvent. Preferably the hydrogen fluoride is added to said zeolite as a solution of hydrofluoric acid in distilled water. The method of preparing these HF-modified catalysts is illustrated in the accompanying Example 1.

For example, the treatment of the Y-zeolites with fluoride ion is accomplished by adding a solution of from one to about 60% or one N to 30N fluoride compound such as, for example, hydrogen fluoride, ammonium fluoride, triflic acid, fluorosulfonic acid or triflic anhydride in distilled water or an organic solvent such as a ketone, such as acetone, to 100 g of a Y-zeolite or dealuminated Y-zeolite, stirring from 1 hour to at least 24 hours, under nitrogen, filtering and washing the solids with distilled water, then drying in vacuo at 40° C. overnight plus 150° C. for 4 hours.

Said catalysts should have a residual acidity in the range 0.1 to 100 mg KOH/g and they may be in the form of powders, pellets, granules, spheres, shapes and extrudates. The examples described herein demonstrate the advantages of using extrudates.

The reaction may be carried out in either a stirred slurry reactor or in a fixed bed continuous flow reactor. The catalyst concentration should be sufficient to provide the desired catalytic effect.

Etherification (Eq. 2) and dehydration (Eq. 3) can generally be conducted at temperatures from 20° to 300° C.; the preferred range is 120° to 250° C. and the most preferred range is 180° to 220° C. The total operating pressure may be from 0 to 1000 psig, or higher. The preferred pressure range is 50 to 500 psig.

In certain circumstances, it may be particularly desirable that the tBA conversion be high enough (e.g. 80% or greater), such that the crude product mix phase separates into an isobutylene-MTBE product-rich phase and a heavier aqueous methanol phase. Preferably such a product phase separation would be achieved at as low an etherification temperature as possible, but particularly in the range 160°-240° C.

Typically, MTBE is generated continuously in up to ca. 30 wt % concentration or greater in the crude liquid product at total liquid hourly space velocities (LHSV) of up to 6 or higher and relatively mild conditions, where:

$$LHSV = \frac{\text{Volume Of Total Liquid Feed Run Through The Reactor Per Hour}}{\text{Volume of Catalyst In Reactor}}$$

Conversions of t-butanol (tBA, wt %) are estimated in the following examples using the equation:

$$\frac{(\text{Wt \% Conc. of tBA in Feed} - \text{Wt \% Conc. of tBA in Product})}{\text{Wt \% Conc. of tBA in Feed}} \times 100$$

Selectivities for methyl t-butyl ether (MTBE, mole %) and isobutylene (C$_4$H$_8$, mole %) are estimated from:

$$\frac{\text{Moles of } MTBE \text{ (or C}_4\text{H}_8\text{) in Product}}{\text{moles of tBA converted}} \times 100$$

The results in Tables 1-10 illustrate the additional cosynthesis of isobutylene and MTBE from a crude aqueous t-butanol/methanol feedstock comprising four principal components, viz-water, t-butanol, methanol and isopropanol (2-PrOH) in a second etherification unit, using as catalysts:

HF-treated Y-zeolites (Examples 3, 5 and 6);
Triflic acid-treated Y-zeolites (Examples 4 and 7);
Ammonium fluoride-treated Y-zeolites (Examples 8-11); and
Triflic anhydride-treated Y-zeolite (Example 12).

By-product identifications in Tables 1-10 are as follows: Diisobutylene (C$_8$H$_{16}$), isopropyl t-butyl ether (IPTBE) and dimethyl ether (DME).

The preferred catalysts typically show:
a) >90% t-butanol conversion per pass.
b) 98% or better molar selectivity to isobutylene plus MTBE.
c) Very little cogeneration of diisobutylene or isopropyl t-butyl ether (IPTBE).
d) Controlled quantities of dimethyl ether formation.
e) Product phase separation into an isobutylene/MTBE product phase and an aqueous methanol heavier phase at operating temperatures of 160° C. or above.

Extended catalyst life (2000 hours) is illustrated in Tables 11-14 and Examples 13 and 14 for both an ammonium fluoride-treated Y-zeolite (LZY-82) and a hydrofluoric acid treated Y-zeolite (CP316-26).

The same, untreated Y-zeolite (CP316-26) shows poor performance with the same feedstock, and under the same conditions, in the comparative Example A and Table 15.

Ethyl t-butyl ether (ETBE) production from crude t-butanol plus ethanol using the fluoride-treated Y-zeolite catalyst of Example 1, is illustrated in Example 15.

The examples which follow illustrate the second stage synthesis of MTBE and isobutylene from crude t-butanol/methanol feedstocks using acidic, fluoride-treated Y-type zeolites, particularly in the form of extrudates. The examples are only intended as a means of illustration and it is understood the invention is not meant to be limited thereby.

EXAMPLE 1

This example illustrates the preparation of a hydrogen fluoride-modified Y-zeolite.

To 100 g of Y-zeolite (CP316-26, an ammonium-exchanged, thermally-stabilized Y-zeolite having a silica:alumina ratio of 46 and a unit cell size of 24.26A, in 1/16" diameter extruded form) was added a solution of 48% hydrofluoric acid (50 g) in distilled water (100 g). The mixture was stirred overnight, under nitrogen, filtered and the solids washed with distilled water, then dried in vacuo at 40° C., overnight, plus 150° C. for 4 hours.

The recovered white extrudates were found to comprise on analysis:

| |
|---|
| Fluoride, 4.7% |
| Water, 1.9% |
| Acidity, 4.8 mg KOH/g |

EXAMPLE 2

To 100 g of Y-zeolite (Cp316-26 that had been dried in vacuo at 175° C. for 3 hours and had a water content of 0.54%) was added a solution of trifluoromethane sulfonic acid (40 g), in dried acetone, (40 cc, dried over 4Å sieve). The mixture was stirred overnight under nitrogen, filtered and the solids washed with dried acetone then dried in vacuo at 40° C. overnight, plus at 150° C. for 4 hours.

The recovered reddish-brown extrudates were found to comprise by analysis:

| |
|---|
| Water, 1.33% |
| Acidity, 29.7 mg KOH/g |

EXAMPLE 3

This example illustrates the cosynthesis of isobutylene and MTBE from a crude aqueous t-butanol/methanol feedstock using a hydrogen fluoride-modified Y-zeolite.

Synthesis was conducted in a tubular reactor (½" id, 12" long) constructed of 316 stainless steel, operated upflow and mounted in a furnace controllable to ±1.0° C. and fitted with pumps allowing flow control to ±1 cc/hr. The reactor was also fitted with a pressure regulating device and equipment for monitoring temperature, pressure and flow rate.

The reactor was charged at the beginning of the experiment with 25 cc of hydrogen fluoride-treated Y-zeolite extrudates, prepared by the method of Example 1. A screen of glass wool was placed at the top and bottom of the reactor to ensure the catalyst would remain in the middle portion.

The catalyst bed was treated with a crude t-butanol/methanol feed mix also containing sizeable quantities of water and isopropanol components, upflow, at a feed rate of 50 cc/hr, while the reactor was held at 140° C. with a total pressure of 300 psi. Samples of effluents were collected periodically on stream and analyzed by glc and gc-ir.

Typical analyses data for samples taken under these conditions are summarized in Table 1. Performance at higher temperatures (160°, 180°, 200° C.) was determined using the same procedures. These results are also given in Table 1.

Operating at 200° C., where the effluent comprises two phases, the t-butanol conversion level and isobutylene/MTBE selectivities are as follows:

t-Butanol conversion = 94%
Isobutylene selectivity = 91 mole %
MTBE selectivity = 7 mole %

TABLE 2

| Ex. | Catalyst | Feed Rate (cc/hr) | Temp. (°C.) | Time On Stream (Days) | Sample | PRODUCT COMPOSITION (WT %) METHOD 26 | | | | | | METHOD 27 | | |
|---|---|---|---|---|---|---|---|---|---|---|---|---|---|---|
| | | | | | | H₂O | MeOH | 2-PrOH | C₄H₈ | tBA | MTBE | C₈H₁₆ | IPTBE | DME |
| 3 | Ex. 1 | 50 | | | FS-1 | 25.7 | 36.0 | 11.7 | — | 26.5 | | | | |
| | | | 140 | 1 | 1 | 31.4 | 31.3 | 11.5 | 2.1 | 11.7 | 12.0 | 0.2 | 0.2 | — |
| | | | | | 2 | 31.4 | 31.3 | 11.5 | 2.1 | 11.7 | 12.0 | 0.2 | 0.2 | — |
| | | | 160 | | 3 | 31.9 | 32.2 | 11.5 | 3.8 | 9.8 | 10.6 | 1.0 | 0.2 | 0.12 |
| | | | | 2 | 4 | 32.4 | 32.1 | 11.5 | 3.8 | 9.7 | 10.4 | 1.3 | 0.2 | 0.08 |
| | | | 180 | 3 | 5 | $^a$ 38.5 | 37.0 | 120 | 3.9 | 4.0 | 4.6 | 0.1 | 0.1 | 0.11 |
| | | | | | 6 | $^a$ 36.4 | 37.4 | 12.1 | 4.3 | 4.9 | 5.0 | 0.1 | 0.1 | 0.07 |
| | | | 180 | R-1 | $^b$R-2 | 15.4 | 18.9 | 8.8 | 43.4 | 2.1 | 11.0 | 3.5 | 0.3 | 0.60 |
| | | | | | | 39.0 | 39.4 | 12.3 | 3.1 | 2.9 | 3.3 | 0.1 | — | — |
| | | | 200 | 4 | 7 | $^a$ 39.0 | 41.5 | 12.7 | 3.0 | 2.1 | 1.6 | — | — | 0.24 |
| | | | | | $^d$8 | $^a$ 38.7 | 41.6 | 12.8 | 3.1 | 2.2 | 1.6 | — | — | 0.48 |
| | | | 200 | R-2 | R-2 | 12.2 | 13.2 | 8.4 | 59.3 | 1.0 | 5.1 | 4.1 | 0.1 | 1.2 |
| | | | | | | 41.5 | 42.0 | 11.1 | 2.3 | 1.9 | 1.1 | 0.1 | — | — |

$^a$Insufficient sample for analysis
$^b$Relative size of phases, 1:3.3 (t/b)

EXAMPLE 4

This example illustrates the cosynthesis of isobutylene and MTBE from a crude aqueous t-butanol/methanol feedstock using a triflic acid-modified Y-zeolite.

Using the equipment and procedures of Example 3, the reactor was charged with 25 cc of triflic acid-treated Y-zeolite extrudates, prepared by the method of Example 2. The catalyst bed was then treated with a crude t-butanol/methanol feedstock also containing sizeable quantities of water and isopropanol at four different operating temperatures (140°, 160°, 180° and 200° C.). Typical product analyses data are given in Table 2.

Operating at 200° C., where the effluent comprises two phases, the t-butanol conversion level and isobutylene/MTBE selectivities are as follows:

t-Butanol conversion = 94%
Isobutylene selectivity = 90%
MTBE selectivity = 9%

TABLE 2

| Ex. | Catalyst | Feed Rate (cc/hr) | Temp. (°C.) | Time On Stream (Days) | Sample | PRODUCT COMPOSITION (WT %) METHOD 26 | | | | | | METHOD 27 | |
|---|---|---|---|---|---|---|---|---|---|---|---|---|---|
| | | | | | | H₂O | MeOH | 2-PrOH | C₄H₈ | tBA | MTBE | C₈H₁₆ | IPTBE |
| 4 | Ex. 2 | 50 | | | FS-1 | 26.5 | 36.0 | 11.6 | | 25.9 | | | |
| | | | 140 | 1 | 1 | 31.1 | 32.2 | 11.7 | 2.1 | 11.6 | 11.3 | 0.3 | 0.2 |
| | | | | | 2 | 30.6 | 32.1 | 11.7 | 2.1 | 11.8 | 11.6 | 0.3 | 0.2 |
| | | | 160 | 2 | 3 | 31.9 | 33.5 | 11.8 | 3.9 | 9.4 | 9.4 | 2.0 | 0.2 |
| | | | | | 4 | 31.8 | 33.3 | 11.8 | 3.8 | 9.3 | 10.1 | 1.9 | 0.2 |
| | | | 180 | 3 | 5 | $^c$ 36.7 | 39.7 | 12.4 | 3.1 | 3.9 | 4.1 | 0.4 | 0.1 |
| | | | | | $^a$6 | 16.5 | 20.0 | 9.3 | 39.8 | 2.6 | 11.4 | 5.8 | 0.3 |

TABLE 2-continued

| Ex. | Catalyst | Feed Rate (cc/hr) | Temp. (°C.) | Time On Stream (Days) | Sample | PRODUCT COMPOSITION (WT %) | | | | | | | |
|---|---|---|---|---|---|---|---|---|---|---|---|---|---|
| | | | | | | METHOD 26 | | | | | | METHOD 27 | |
| | | | | | | H₂O | MeOH | 2-PrOH | C₄H₈ | tBA | MTBE | C₈H₁₆ | IPTBE |
| | | | | | | 38.5 | 39.9 | 12.1 | 2.8 | 3.4 | 3.3 | 0.2 | — |
| | | | 200 | 4 | 7 { c / 40.2 | | 42.3 | 11.7 | 2.4 | 2.1 | 1.3 | — | 0.1 |
| | | | | | ᵇ8 { 8.9 | | 10.8 | 7.1 | 65.5 | 1.0 | 6.0 | 0.1 | 1.1 |
| | | | | | 39.9 | | 42.3 | 12.0 | 2.6 | 1.9 | 1.3 | — | — |

ᵃRelative size of phases, 1:5.0 (t/b)
ᵇRelative size of phases, 1:3.3 (t/b)
ᶜInsufficient sample for analysis

EXAMPLES 5-12

These examples also illustrate the cosynthesis of isobutylene and MTBE from crude aqueous t-butanol/methanol feedstocks using various fluoride-treated Y-zeolites.

Using the equipment and procedures of Example 3, the following classes of fluoride-treated Y-zeolites were evaluated:

a) Hydrofluoric acid-treated Linde SK-500 (Table 3).
b) Hydrofluoric acid-treated CP304-37 from PQ Corp. (Table 4).
c) Triflic acid-treated Linde SK-500 (Table 5).
d) Ammonium fluoride-treated LZY-82 from UOP (Tables 6 and 7).
e) Ammonium fluoride-treated LZY-85 from UOP (Tables 8 and 9).
f) Triflic anhydride-treated SK-500 (Table 10).

High (>90%) t-butanol conversions were achieved with most of these catalysts at the higher operating temperatures. Typical t-butanol conversion levels were as follows:

| Ex. | Catalyst Composition | Operation Temp (°C.) | tBA Conversion (%) |
|---|---|---|---|
| 7 | Triflic acid/SK-500 | 200 | 91 |
| 8 | NH₄F/Y-82 | 200 | 93 |
| 9 | NH₄F/Y-85 | 200 | 93 |

TABLE 3

| Ex. | Catalyst | Feed Rate (cc/hr) | Temp. (°C.) | Time On Stream (Days) | Sample | PRODUCT COMPOSITION (WT %) | | | | | | | |
|---|---|---|---|---|---|---|---|---|---|---|---|---|---|
| | | | | | | METHOD 26 | | | | | | METHOD 27 | |
| | | | | | | H₂O | MeOH | 2-PrOH | C₄H₈ | tBA | MTBE | C₈H₁₆ | IPTBE |
| 5 | 6798-4-IRᵃ | 50 | | | FS-1 | 26.2 | 36.2 | 11.6 | | 26.0 | | — | — |
| | | | 140 | 1 | 1 | 29.8 | 33.2 | 11.6 | 1.8 | 15.2 | 8.3 | — | 0.2 |
| | | | | | 2 | 30.0 | 33.1 | 11.7 | 1.9 | 14.8 | 8.5 | — | 0.2 |
| | | | 160 | 2 | 3 | 30.7 | 32.9 | 11.7 | 3.3 | 12.0 | 9.3 | — | 0.2 |
| | | | | | 4 | 30.7 | 33.1 | 11.8 | 3.2 | 12.3 | 9.0 | — | 0.2 |
| | | | 180 | 3 | →5 | 30.5 | 33.1 | 11.5 | 7.8 | 9.3 | 7.6 | — | 0.2 |
| | | | | | 6 | 30.7 | 33.6 | 11.7 | 6.4 | 10.3 | 7.2 | — | 0.2 |
| | | | | | 6-2 | 27.3 | 35.4 | 11.5 | 0.4 | 24.6 | 0.8 | — | 0.1 |
| | | | 200 | 4 | →7 { ᵇ / 35.4 | | 37.6 | 12.4 | 4.5 | 5.0 | 5.0 | — | 0.1 |
| | | | | | 8 { ᵇ / 36.2 | | 37.2 | 12.3 | 4.3 | 5.1 | 4.8 | — | 0.1 |
| | | | | | ᶜ8-1 { 8.8 | | 14.3 | 7.7 | 49.1 | 3.8 | 15.9 | — | — |
| | | | | | 36.0 | | 38.0 | 12.4 | 4.0 | 4.8 | 4.8 | — | 0.1 |

ᵃHF-treated SK-500, 1/16"
ᵇInsufficient sample for analysis
ᶜRealtive sizes of two phases, 1:5.5 (t/b)

TABLE 4

| Ex. | Catalyst | Feed Rate (cc/hr) | Temp. (°C.) | Time On Stream (Days) | Sample | PRODUCT COMPOSITION (WT %) | | | | | | | |
|---|---|---|---|---|---|---|---|---|---|---|---|---|---|
| | | | | | | METHOD 26 | | | | | | METHOD 27 | |
| | | | | | | H₂O | MeOH | 2-PrOH | C₄H₈ | tBA | MTBE | C₈H₁₆ | IPTBE |
| 6 | 6798-7ᵃ | 50 | | | FS-1 | 26.3 | 35.7 | 11.7 | | 26.1 | | — | — |
| | | | 140 | 1 | 1 | 30.6 | 31.8 | 11.7 | 2.1 | 12.6 | 11.2 | 0.1 | 0.2 |
| | | | | | 2 | 30.2 | 31.9 | 11.8 | 2.2 | 12.5 | 11.4 | 0.1 | 0.2 |
| | | | 160 | 2 | 3 | 30.6 | 32.5 | 11.7 | 3.9 | 10.6 | 10.7 | 0.6 | 0.2 |
| | | | | | 4 | 31.2 | 32.5 | 11.8 | 3.9 | 10.2 | 10.3 | 0.5 | 0.2 |
| | | | 180 | 3 | 5 | 32.3 | 34.0 | 11.7 | 6.4 | 8.4 | 6.9 | — | 0.2 |
| | | | | | 6 | 30.3 | 33.0 | 11.6 | 7.9 | 9.7 | 7.5 | — | 0.3 |
| | | | | 4 | 7 { ᵇ / 37.3 | | 39.9 | 12.9 | 3.9 | 3.1 | 2.9 | — | — |
| | | | | | | 14.0 | 18.0 | 7.7 | 48.9 | 2.3 | 9.0 | 0.1 | 0.2 |

TABLE 4-continued

| Ex. | Catalyst | Feed Rate (cc/hr) | Temp. (°C.) | Time On Stream (Days) | Sample | PRODUCT COMPOSITION (WT %) METHOD 26 | | | | | | METHOD 27 | |
|---|---|---|---|---|---|---|---|---|---|---|---|---|---|
| | | | | | | $H_2O$ | MeOH | 2-PrOH | $C_4H_8$ | tBA | MTBE | $C_8H_{16}$ | IPTBE |
| | | | 200 | | c8 { 38.2 | 39.5 | 12.8 | 3.4 | 3.3 | 2.8 | — | — | |

*a*HF on CP304-37, 1/16" E
*b*Insufficient sample for analysis
*c*Relative sizes of phases, 1:3.5 (t/b)

TABLE 5

| Ex. | Catalyst | Feed Rate (cc/hr) | Temp. (°C.) | Time On Stream (Days) | Sample | PRODUCT COMPOSITION (WT %) METHOD 26 | | | | | | METHOD 27 | |
|---|---|---|---|---|---|---|---|---|---|---|---|---|---|
| | | | | | | $H_2O$ | MeOH | 2-PrOH | $C_4H_8$ | tBA | MTBE | $C_8H_{16}$ | IPTBE |
| 7 | 6798-3*a* | 50 | | | FS-1 | 26.4 | 36.0 | 11.6 | | 25.9 | | — | — |
| | | | 140 | 1 | 1 | 30.7 | 32.4 | 11.7 | 2.1 | 12.3 | 10.9 | — | 0.2 |
| | | | | | 2 | 30.6 | 32.5 | 11.7 | 2.0 | 12.5 | 10.7 | — | 0.2 |
| | | | 160 | 2 | 3 | 31.1 | 32.7 | 11.7 | 3.7 | 10.4 | 10.3 | 0.1 | 0.2 |
| | | | | | 4 | 31.5 | 33.0 | 11.8 | 3.7 | 10.3 | 9.9 | 0.1 | 0.2 |
| | | | 180 | 3 | 5 { b | | | | | | | | |
| | | | | | { 34.5 | 36.2 | 11.9 | 5.3 | 6.4 | 5.7 | — | 0.2 | |
| | | | | | d6 { b | | | | | | | | |
| | | | | | { 33.5 | 35.4 | 11.8 | 5.9 | 7.3 | 6.0 | — | 0.2 | |
| | | | 180 | R-1 | cR-2 { 19.7 | 24.2 | 10.0 | 27.6 | 5.6 | 12.7 | 0.1 | 0.5 | |
| | | | | | { 34.8 | 35.8 | 11.9 | 4.9 | 6.8 | 5.7 | — | 0.1 | |
| | | | 200 | | 7 { b | | | | | | | | |
| | | | | | { 37.1 | 38.8 | 12.5 | 3.9 | 3.9 | 3.7 | — | 0.1 | |
| | | | | | 8 { b | | | | | | | | |
| | | | | | { 34.2 | 36.3 | 11.9 | 5.6 | 6.7 | 5.3 | — | 0.1 | |
| | | | 200 | R-2 | R-4 { 14.6 | 18.2 | 7.4 | 50.8 | 1.6 | 7.2 | — | 0.2 | |
| | | | | | { 38.1 | 40.5 | 12.9 | 3.4 | 2.6 | 2.3 | — | — | |

*a*Triflic acid-treated SK-500, 1/16" E
*b*Insufficient sample for analysis
*c*Relative sizes of phases, 1:7.7 (t/b)

TABLE 6

| Ex. | Catalyst | Feed Rate (cc/hr) | Temp. (°C.) | Time On Stream (Days) | Sample | PRODUCT COMPOSITION (WT %) METHOD 26 | | | | | | METHOD 27 | |
|---|---|---|---|---|---|---|---|---|---|---|---|---|---|
| | | | | | | $H_2O$ | MeOH | 2-PrOH | $C_4H_8$ | tBA | MTBE | $C_8H_{16}$ | IPTBE |
| 8 | 2143-CT-90*a* | 50 | | | FS-1 | 26.5 | 36.0 | 11.6 | | 26.0 | | | |
| | | | 140 | 1 | 1 | 30.3 | 32.1 | 11.5 | 2.1 | 11.9 | 11.9 | | |
| | | | | | →2 | 30.1 | 31.9 | 11.5 | 2.2 | 11.7 | 12.5 | | |
| | | | 160 | 2 | 3 | 32.4 | 34.2 | 11.8 | 3.1 | 9.2 | 9.2 | | |
| | | | | | 4 | 32.5 | 34.2 | 11.9 | 3.1 | 9.2 | 9.2 | | |
| | | | 180 | 3 | 5 { b | | | | | | | | |
| | | | | | { 38.8 | 39.7 | 11.9 | 2.6 | 3.4 | 3.5 | 0.1 | 0.1 | |
| | | | | | →6 { e | | | | | | | | 0.1 |
| | | | | | { 38.5 | 40.1 | 11.9 | 2.8 | 3.2 | 3.5 | 0.1 | 0.1 | |
| | | | 180 | R-1 | R-2 { 18.6 | 23.1 | 9.8 | 31.0 | 4.6 | 12.8 | — | | |
| | | | | | { 36.3 | 36.5 | 12.2 | 4.6 | 5.0 | 5.3 | — | 0.1 | |
| | | | 200 | 4 | 7 { b | | | | | | | | |
| | | | | | { 39.3 | 41.8 | 12.4 | 3.0 | 1.9 | 1.5 | — | — | |
| | | | | | 8 { b | | | | | | | | |
| | | | | | { 38.3 | 42.1 | 12.7 | 3.1 | 2.2 | 1.6 | — | — | |
| | | | 200 | R-2 | R-4 { 12.2 | 16.0 | 7.1 | 57.4 | 1.4 | 5.8 | — | 0.2 | |
| | | | | | { 38.2 | 42.2 | 13.4 | 2.5 | 1.9 | 1.7 | — | — | |

*a*UOP's Y-82 zeolite, $NH_4F$ treated, 6 hours, 1/16" E
*b*Insufficient sample for analysis

TABLE 7

| Ex. | Catalyst | Feed Rate (cc/hr) | Temp. (°C.) | Time On Stream (Days) | Sample | H₂O | MeOH | 2-PrOH | C₄H₈ | tBA | MTBE | C₈H₁₆ | IPTBE |
|---|---|---|---|---|---|---|---|---|---|---|---|---|---|
| | | | | | | \multicolumn{6}{c|}{METHOD 26} | \multicolumn{2}{c}{METHOD 27} | |
| 9 | 2143-CT-90[a] | 50 | | | FS-1 | 26.0 | 35.9 | 11.7 | | 26.4 | | | |
| | | | 140 | 1 | 1 | 31.0 | 31.3 | 11.5 | 2.3 | 11.2 | 12.7 | 0.4 | 0.2 |
| | | | | | 2 | 30.9 | 31.2 | 11.5 | 2.3 | 11.0 | 12.8 | 0.4 | 0.2 |
| | | | 160 | 2 | 3 | 33.0 | 33.2 | 11.7 | 3.3 | 9.0 | 9.8 | 2.2 | 0.2 |
| | | | | | 4 | 32.0 | 31.2 | 11.1 | 3.0 | 12.6 | 10.0 | 2.2 | 0.2 |
| | | | 180 | 3 | 5 { | 2.2 | 8.5 | 9.1 | 58.1 | 2.5 | 17.2 | 0.2 | — |
| | | | | | | 41.2 | 38.2 | 11.6 | 2.7 | 3.0 | 3.6 | | |
| | | | | | 6 { | b | 39.4 | 11.8 | 2.8 | 3.1 | 3.3 | — | — |
| | | | | | | 39.2 | | | | | | | |
| | | | 180 | R-1 | [c]R-2 { | 4.5 | 9.7 | 6.2 | 53.8[b] | 5.6[b] | 17.7[b] | 0.5 | 0.5 |
| | | | | | | 36.0 | 36.4 | 12.1 | 4.5 | 5.6 | 5.3 | — | 0.1 |
| | | | 200 | 4 | 7 { | b | 40.8 | 12.0 | 2.8 | 2.1 | 1.6 | — | — |
| | | | | | | 40.6 | | | | | | | |
| | | | | | 8 { | b | 41.0 | 12.3 | 3.0 | 2.1 | 1.7 | — | — |
| | | | | | | 39.9 | | | | | | | |
| | | | 200 | R-2 | [d]R-4 { | 11.7 | 15.0 | 6.6 | 59.5 | 1.3 | 5.9 | 0.2 | 0.1 |
| | | | | | | 39.1 | 41.5 | 12.7 | 3.1 | 2.0 | 1.6 | — | — |

[a]UOP's Y-82 zeolite, NH₄F treated, 3 hours, 1/16" E
[b]Insufficient sample for analyses
[c]Relative sizes of phases, 1:5.5 (t/b)
[d]Relative sizes of phases, 1:2.9 (t/b)

TABLE 8

| Ex. | Catalyst | Feed Rate (cc/hr) | Temp. (°C.) | Time On Stream (Days) | Sample | H₂O | MeOH | 2-PrOH | C₄H₈ | tBA | MTBE | C₈H₁₆ | IPTBE |
|---|---|---|---|---|---|---|---|---|---|---|---|---|---|
| | | | | | | \multicolumn{6}{c|}{METHOD 26} | \multicolumn{2}{c}{METHOD 27} | |
| 10 | 2042-CT-90[a] | 50 | | | FS-1 | 26.4 | 36.1 | 11.6 | | 26.0 | | | |
| | | | 140 | 1 | 1 | 28.7 | 33.3 | 11.6 | 1.5 | 21.5 | 3.3 | — | 0.1 |
| | | | | | 2 | 28.4 | 34.6 | 11.6 | 1.8 | 19.3 | 4.3 | — | — |
| | | | 160 | 2 | 3 | 30.4 | 32.3 | 11.5 | 3.5 | 14.1 | 8.1 | — | 0.2 |
| | | | | | 4 | 30.7 | 32.5 | 11.4 | 2.8 | 17.1 | 5.5 | — | 0.1 |
| | | | 180 | 3 | 5 | 28.6 | 34.3 | 11.5 | 1.0 | 23.1 | 1.5 | — | — |
| | | | | | 6 | 28.3 | 34.6 | 11.5 | 0.8 | 23.7 | 1.1 | — | — |
| | | | 180 | R-1 | R-2 | 27.1 | 35.3 | 11.7 | 0.4 | 15.2 | 0.3 | — | — |
| | | | 200 | 4 | 7 | 29.6 | 34.1 | 11.5 | 2.5 | 20.1 | 2.2 | — | 0.1 |
| | | | | | 8 | 20.4 | 34.3 | 11.4 | 2.0 | 21.1 | 1.8 | — | 0.1 |
| | | | | R-2 | R-4 | 28.2 | 34.7 | 11.7 | 1.3 | 23.1 | 0.9 | — | — |

[a]UOP's Y-85 zeolite, NH₄F treated, 6 hours, 1/16 E

TABLE 9

| Ex. | Catalyst | Feed Rate (cc/hr) | Temp. (°C.) | Time On Stream (Days) | Sample | H₂O | MeOH | 2-PrOH | C₄H₈ | tBA | MTBE | C₈H₁₆ | IPTBE |
|---|---|---|---|---|---|---|---|---|---|---|---|---|---|
| | | | | | | \multicolumn{6}{c|}{METHOD 26} | \multicolumn{2}{c}{METHOD 27} | |
| 11 | 2140-CT-90[a] | 50 | | | FS-1 | 26.2 | 35.9 | 11.7 | | 26.2 | | | |
| | | | 140 | 1 | 1 | 30.5 | 31.8 | 11.7 | 2.0 | 12.9 | 10.8 | 0.1 | 0.2 |
| | | | | | 2 | 29.5 | 32.3 | 11.8 | 2.0 | 13.4 | 10.7 | 0.1 | 0.2 |
| | | | 160 | 2 | 3 | 31.4 | 32.5 | 11.8 | 3.7 | 10.5 | 10.2 | 0.7 | 0.2 |
| | | | | | 4 | 30.5 | 32.6 | 11.8 | 3.6 | 10.9 | 10.6 | 0.6 | 0.2 |
| | | | 180 | 3 | 5 { | d | 34.9 | 12.0 | 6.6 | 7.5 | 6.9 | 0.1 | 0.1 |
| | | | | | | 32.1 | | | | | | | |
| | | | | | [b]6 { | 5.8 | 14.0 | 8.7 | 46.1 | 6.6 | 18.6 | 0.2 | 0.2 |
| | | | | | | 33.3 | 35.5 | 12.0 | 5.6 | 7.2 | 6.4 | — | 0.1 |
| | | | 200 | 4 | 7 { | d | 39.6 | 12.7 | 3.8 | 3.3 | 3.2 | — | — |
| | | | | | | 37.4 | | | | | | | |
| | | | | | [c]8 { | 7.8 | 12.2 | 6.6 | 59.5 | 2.2 | 11.6 | 0.2 | 0.3 |

TABLE 9-continued

| Ex. | Catalyst | Feed Rate (cc/hr) | Temp. (°C.) | Time On Stream (Days) | Sample | PRODUCT COMPOSITION (WT %) METHOD 26 | | | | | | METHOD 27 | | |
|---|---|---|---|---|---|---|---|---|---|---|---|---|---|---|
| | | | | | | $H_2O$ | MeOH | 2-PrOH | $C_4H_8$ | tBA | MTBE | $C_8H_{16}$ | IPTBE | |
| | | | | | | 38.3 | 39.4 | 12.8 | 3.3 | 3.2 | 3.1 | — | — | |

[a] UOP's Y-85, $NH_4F$ treated, 3 hours, 1/16" E
[b] Relative sizes of phases, 1:12.5 (t:b)
[c] Relative sizes of phases, 1:3.5 (t:b)
[d] Insufficient sample for analyses

TABLE 10

| Ex. | Catalyst | Feed Rate (cc/hr) | Temp. (°C.) | Time On Stream (Days) | Sample | PRODUCT COMPOSITION (WT %) METHOD 26 | | | | | | METHOD 27 | | |
|---|---|---|---|---|---|---|---|---|---|---|---|---|---|---|
| | | | | | | $H_2O$ | MeOH | 2-PrOH | $C_2H_8$ | tBA | MTBE | $C_8H_{16}$ | IPTBE | DME |
| 12 | 6798-41[a] | 50 | | | FS-1 | 26.4 | 35.8 | 11.7 | | 26.1 | | | | |
| | | | 160 | 1 | 1 | 30.9 | 32.2 | 11.7 | 4.0 | 10.4 | 10.8 | 0.1 | 0.2 | 0.07 |
| | | | | | 2 | 31.4 | 32.3 | 11.8 | 4.2 | 9.9 | 10.4 | 0.1 | 0.2 | 0.07 |
| | | | 180 | 2 | 3 {[b] | | 36.8 | 12.2 | 4.2 | 4.8 | 5.2 | — | 0.1 | 0.06 |
| | | | | | | 36.9 | | | | | | | | |
| | | | | | [c]4 { | 15.3 | 20.4 | 9.3 | 35.4 | 4.9 | 14.5 | 0.1 | 0.5 | 0.05 |
| | | | | | | 36.2 | 36.2 | 12.1 | 4.7 | 5.3 | 5.6 | — | 0.1 | 0.04 |
| | | | 200 | 3 | 5 {[b] | | 39.8 | 12.8 | 3.8 | 3.5 | 3.1 | — | — | 0.02 |
| | | | | | | 36.9 | | | | | | | | |
| | | | | | [d]6 { | 14.3 | 18.6 | 8.2 | 45.2 | 2.9 | 10.7 | — | 0.3 | 0.02 |
| | | | | | | 36.9 | 38.8 | 12.6 | 3.9 | 3.9 | 3.8 | — | 0.1 | 0.02 |

[a] Triflic anhydride on Linde SK-500
[b] Insufficient sample for analysis
[c] Relative sizes of phases, 1:6.5 (t:b)
[d] Relative sizes of phases, 1:4.2 (t:b)

EXAMPLE 13

Following the procedures and using the equipment of Example 3, a sample of ammonium fluoride-treated Y-zeolite (UOP's LZY-82) was treated with a crude t-butanol/methanol feed mix, also containing sizeable quantities of water and isopropanol components, at 200°–220° C. for a period of 84 days (ca. 2000 hours). Typical product analyses data are given in Tables 11 and 12 for these two-phase products. Summary t-butanol conversion and isobutylene/MTBE selectivities are as follows:

| Sample | Time On Stream (Days) | t-Butanol Conv (%) | Molar Selectivities | |
|---|---|---|---|---|
| | | | $C_4H_8$ | MTBE |
| 2R | 2 | 93 | 89 | 8.7 |
| 6 | 17 | 89 | 81 | 14 |
| 14 | 52 | 92 | 88 | 12 |
| 18 | 81 | 82 | 80 | 24 |

TABLE 11

| Ex. | Catalyst | Feed Rate (cc/hr) | Temp. (°C.) | Time On Stream (Days) | Sample | PRODUCT COMPOSITION (WT %) METHOD 26 | | | | | | METHOD 27 | | |
|---|---|---|---|---|---|---|---|---|---|---|---|---|---|---|
| | | | | | | $H_2O$ | MeOH | 2-PrOH | $C_2H_8$ | tBA | MTBE | $C_8H_{16}$ | IPTBE | DME |
| 13 | 2143-CT-90[a] | 50 | | | FS-1 | 26.2 | 36.0 | 11.7 | | 26.1 | | | | |
| | | | 200 | 1 | 1[b] { | 7.1 | 11.4 | 7.2 | 63.1 | 1.7 | 9.2 | c | c | c |
| | | | | | | 39.7 | 41.6 | 12.5 | 2.9 | 1.9 | 1.4 | — | — | 0.22 |
| | | | | 2 | →2R[d] { | 14.9 | 17.7 | 7.2 | 53.7 | 1.2 | 5.1 | 0.6 | 0.1 | 0.15 |
| | | | | | | 38.6 | 41.8 | 12.8 | 3.0 | 2.1 | 1.6 | — | — | 0.26 |
| | | | | 4 | 3[e] { | 13.7 | 17.2 | 7.2 | 54.1 | 1.5 | 6.2 | 0.2 | 0.2 | 0.07 |
| | | | | | | 38.2 | 41.7 | 13.1 | 3.2 | 2.1 | 1.8 | — | — | 0.05 |
| | | | | 7 | 4[f] { | 11.4 | 14.8 | 6.6 | 58.9 | 1.4 | 6.7 | 0.1 | 0.2 | 0.04 |
| | | | | | | 37.7 | 41.4 | 13.0 | 3.3 | 2.6 | 1.9 | — | — | 0.04 |
| | | | | 13 | 5[g] { | 11.7 | 15.3 | 6.9 | 56.7 | 1.7 | 7.7 | 0.1 | 0.2 | 0.03 |
| | | | | | | 38.0 | 40.6 | 12.9 | 3.5 | 2.8 | 2.2 | — | — | 0.03 |
| | | | | | FS-2 | 26.1 | 35.6 | 11.6 | | 26.1 | | | | |
| | | | | 17 | →6[h] { | 12.6 | 16.6 | 7.2 | 58.8 | 2.0 | 8.8 | 0.1 | 0.2 | 0.02 |
| | | | | | →7 { | 38.0 | 40.1 | 12.8 | 3.4 | 3.0 | 2.7 | — | — | 0.02 |
| | | | | 20 | 8 | 31.2 | 33.9 | 11.7 | 6.9 | 9.7 | 6.5 | — | 0.2 | 0.01 |
| | | [i] | | 25 | | 30.1 | 34.4 | 11.7 | 5.4 | 12.7 | 5.7 | — | 0.2 | — |

TABLE 11-continued

| Ex. | Catalyst | Feed Rate (cc/hr) | Temp. (°C.) | Time On Stream (Days) | Sample | PRODUCT COMPOSITION (WT %) METHOD 26 | | | | | | METHOD 27 | | |
|---|---|---|---|---|---|---|---|---|---|---|---|---|---|---|
| | | | | | | $H_2O$ | MeOH | 2-PrOH | $C_2H_8$ | tBA | MTBE | $C_8H_{16}$ | IPTBE | DME |
| | | | | i | FS-3 | 26.2 | 35.7 | 12.1 | | 25.9 | | | | |
| | | | 220 | 28 | 9$^k$ | 17.1 | 20.9 | 8.6 | 41.7 | 2.9 | 8.7 | 0.7 | 0.3 | 0.02 |
| | | | | | | 37.2 | 39.0 | 12.9 | 3.8 | 3.9 | 3.2 | 0.1 | — | 0.02 |
| | | | | 31 | 10$^l$ | 13.9 | 17.8 | 7.8 | 49.7 | 2.3 | 8.4 | 0.1 | 0.2 | 0.01 |
| | | | | | | 35.0 | 38.7 | 15.8 | 3.9 | 3.9 | 2.7 | — | — | 0.01 |

$^a$UOP's Y-82 Zeolite, NH$_4$F treated, 6 Hr, 1/16" E
$^b$No data on relative volumes of the two phases
$^c$No analyses data
$^d$Relative sizes of phases, 1:2.8 (t:b)
$^e$Relative sizes of phases, 1:3.2 (t:b)
$^f$Relative sizes of phases, 1:3.5 (t:b)
$^g$Relative sizes of phases, 1:3.9 (t:b)
$^h$Relative sizes of phases, 1:3.5 (t:b)
$^i$unit shut down
$^j$Raise operating temperature
$^k$Relative sizes of phases, 1:3.8 (t:b)
$^l$Relative sizes of phases, 1:3.5 (t:b)

TABLE 12

| Ex. | Catalyst | Feed Rate (cc/hr) | Temp. (°C.) | Time On Stream (Days) | Sample | PRODUCT COMPOSITION (WT %) METHOD 26 | | | | | | METHOD 27 | | |
|---|---|---|---|---|---|---|---|---|---|---|---|---|---|---|
| | | | | | | $H_2O$ | MeOH | 2-PrOH | $C_4H_8$ | tBA | MTBE | $C_8H_{16}$ | IPTBE | DME |
| 13 | 2143-CT-90 | 50 | 220 | 35 | 11$^k$ | 3.0 | 6.8 | 5.3 | 70.6 | 2.0 | 12.2 | 0.1 | 0.3 | 0.02 |
| | | | | | | 40.2 | 38.9 | 12.4 | 2.8 | 3.2 | 2.5 | — | — | 0.01 |
| | | | | | FS-4 | 26.4 | 35.8 | 11.7 | | 26.1 | | | | |
| | | | | 38 | 12$^l$ | 17.7 | 20.9 | 8.1 | 44.2 | 2.0 | 6.9 | 0.1 | 0.2 | 0.02 |
| | | | | | | 38.1 | 40.8 | 12.5 | 3.2 | 3.0 | 2.3 | — | — | 0.01 |
| | | | | 46 | 13$^m$ | 10.5 | 13.9 | 6.4 | 60.8 | 1.4 | 6.8 | — | — | — |
| | | | | | | 37.7 | 41.4 | 13.0 | 3.5 | 2.4 | 2.0 | 0.1 | — | 0.01 |
| | | | | | FS-5 | 26.2 | 36.0 | 11.7 | | 26.1 | | | | |
| | | | | 52 | →14$^l$ | 11.8 | 15.4 | 6.6 | 57.9 | 1.4 | 6.7 | 0.1 | 0.2 | 0.02 |
| | | | | | | 38.0 | 41.1 | 13.0 | 3.5 | 2.3 | 2.0 | — | — | 0.01 |
| | | | | 60 | 15$^l$ | 5.3 | 9.5 | 5.3 | 70.2 | 1.4 | 8.2 | 0.1 | 0.2 | 0.02 |
| | | | | | | 31.7 | 46.0 | 13.5 | 4.2 | 3.0 | 1.6 | — | — | 0.01 |
| | | | | 66 | 16$^e$ | 1.4 | 5.0 | 4.1 | 80.3 | 1.0 | 7.8 | — | 0.1 | 0.02 |
| | | | | | | 34.8 | 42.6 | 13.1 | 4.4 | 2.5 | 2.6 | — | — | 0.01 |
| | | | | | FS-6 | 26.4 | 36.2 | 11.5 | | 25.8 | | | | |
| | | | | | FS-7 | 26.4 | 36.1 | 11.5 | | 25.8 | | | | |
| | | | | 74 | 17$^n$ | 5.7 | 12.7 | 7.2 | 56.1 | 4.4 | 13.7 | — | 0.4 | 0.01 |
| | | | | | | 32.3 | 38.3 | 12.4 | 6.3 | 5.9 | 4.8 | — | 0.1 | 0.01 |
| | | | | 81 | 18$^o$ | 3.4 | 9.1 | 6.3 | 63.4 | 3.4 | 14.2 | — | 0.4 | 0.01 |
| | | | | | | 35.4 | 38.4 | 12.3 | 4.9 | 4.8 | 4.1 | — | 0.1 | 0.01 |
| | | | | 84 | 19$^n$ | 4.0 | 9.9 | 6.6 | 61.3 | 3.9 | 14.1 | — | 0.4 | 0.01 |
| | | | | | | 35.0 | 38.3 | 12.2 | 5.1 | 5.3 | 4.1 | — | 0.1 | 0.01 |

$^m$Relative sizes of phases 1:3.4 (t:b)
$^n$Relative sizes of phases 1:5.4 (t:b)
$^o$Relative sizes of phases 1:4.4 (t:b)

EXAMPLE 14

Following the procedures and using the equipment of Example 3, a sample of hydrofluoric acid-treated Y-zeolite (CP316-26), prepared by the method of Example 1, was treated with the crude t-butanol/methanol feed mix of Examples 3 and 13, at 200°-220° C. for a period of 85 days (2000+ hours). Typical product analyses data are given in Tables 13 and 14 for these two-phase products.

Summary t-butanol conversion and isobutylene/MTBE selectivities are as follows:

| Sample | Time On Stream (Days) | t-Butanol Conv (%) | Molar Selectivities (%) | |
|---|---|---|---|---|
| | | | $C_4H_8$ | MTBE |
| 1 | 1 | 93 | 60 | 7.2 |
| 4 | 19 | 82 | 85 | 18 |
| 14 | 85 | 80 | 84 | 16 |

TABLE 13

| Ex. | Catalyst | Feed Rate (cc/hr) | Temp. (°C.) | Time On Stream (Days) | Sample | PRODUCT COMPOSITION (WT %) METHOD 26 ||||||  METHOD 27 |||
|---|---|---|---|---|---|---|---|---|---|---|---|---|---|---|
| | | | | | | H$_2$O | MeOH | 2-PrOH | C$_4$H$_8$ | tBA | MTBE | C$_8$H$_{16}$ | IPTBE | DME |
| 14 | Ex. 1[a] | 50 | | | FS-1 | 26.4 | 36.2 | 11.5 | | 25.8 | | | | |
| | | | 200 | 1 | →1[b] | 24.5 | 26.1 | 9.6 | 34.0 | 1.5 | 3.8 | 3.0 | 0.1 | 0.80 |
| | | | | | | 39.0 | 42.7 | 11.8 | 3.1 | 1.8 | 1.5 | — | — | 0.58 |
| | | | | 8 | 2 | 31.0 | 35.2 | 11.6 | 7.8 | 9.1 | 5.3 | 0.1 | 0.1 | — |
| | | | | | FS-2 | 26.4 | 36.1 | 11.5 | | 25.8 | | | | |
| | | | | 15 | 3[d] | 7.8 | 12.8 | 6.6 | 60.1 | 3.1 | 9.5 | 0.1 | 0.3 | 0.02 |
| | | | | | | 36.0 | 39.4 | 12.4 | 4.6 | 4.6 | 2.8 | — | — | 0.01 |
| | | | | 19 | →4[e] | 1.2 | 7.0 | 5.8 | 69.8 | 3.3 | 12.5 | — | 0.3 | 0.02 |
| | | | | | | 35.6 | 39.1 | 12.4 | 4.9 | 4.9 | 3.1 | — | 0.1 | 0.01 |
| | | | | 24 | 5[b] | 5.4 | 13.4 | 7.3 | 57.5 | 4.9 | 11.4 | — | 0.3 | 0.01 |
| | | | | | | 28.4 | 38.5 | 12.7 | 8.7 | 6.9 | 4.7 | — | 0.1 | 0.01 |
| | | | | 31 | 6[g] | 6.6 | 13.3 | 7.6 | 53.8 | 5.6 | 13.1 | — | 0.4 | 0.01 |
| | | | | | | 34.1 | 37.3 | 12.1 | 5.5 | 6.8 | 4.1 | — | 0.1 | 0.01 |
| | | | | | FS-3 | 26.0 | 36.3 | 11.6 | | 26.0 | | | | |
| | | | | 38 | 7[h] | 3.4 | 8.1 | 5.4 | 70.4 | 2.4 | 9.9 | — | 0.2 | 0.01 |
| | | | | | | 33.8 | 41.6 | 13.1 | 4.5 | 4.1 | 2.8 | — | — | 0.01 |
| | | | | | FS-4 | 26.5 | 35.6 | 11.4 | | 26.4 | | | | |
| | | | | 45 | 8[i] | 1.4 | 6.6 | 5.5 | 70.6 | 3.4 | 12.1 | — | 0.2 | 0.01 |
| | | | | | | 31.8 | 40.7 | 13.2 | 4.8 | 6.2 | 3.2 | — | — | 0.01 |

[a]HF treated CP316-26, 1/16" E, dried at 240° C.
[b]Relative sizes of phases, 1:30 (t:b)
[c]Raise operating temperature
[d]Relative sizes of phases, 1:4.4 (t:b)
[e]Relative sizes of phases, 1:5.2 (t:b)
[f]Relative sizes of phases, 1:2.2 (t:b)
[g]Relative sizes of phases, 1:7.3 (t:b)
[h]Relative sizes of phases, 1:4.0 (t:b)
[i]Relative sizes of phases, 1:4.6 (t:b)

TABLE 14

| Ex. | Catalyst | Feed Rate (cc/hr) | Temp. (°C.) | Time On Stream (Days) | Sample | PRODUCT COMPOSITION (WT %) METHOD 26 |||||| METHOD 27 |||
|---|---|---|---|---|---|---|---|---|---|---|---|---|---|---|
| | | | | | | H$_2$O | MeOH | 2-PrOH | C$_4$H$_8$ | tBA | MTBE | C$_8$H$_{16}$ | IPTBE | DME |
| 14 | Ex. 1 | 50 | 220 | | FS-1 | 26.5 | 35.8 | 11.6 | | 26.0 | | | | |
| | | | | 53 | →9[j] | 3.0 | 9.2 | 6.3 | 64.0 | 4.0 | 13.4 | — | 0.2 | 0.01 |
| | | | | | | 33.8 | 38.4 | 12.1 | 5.9 | 5.4 | 4.4 | — | — | 0.01 |
| | | | | 57 | 10 | 3.2 | 9.5 | 6.6 | 62.7 | 4.6 | 13.4 | — | — | 0.01 |
| | | | | | | 32.8 | 37.3 | 12.1 | 6.5 | 6.9 | 4.0 | — | — | 0.01 |
| | | | | | FS-6 | 26.4 | 36.1 | 11.6 | | 25.8 | | | | |
| | | | | 68 | 11[g] | l | | | | | | — | 0.4 | 0.01 |
| | | | | | | 33.5 | 36.3 | 11.9 | 6.2 | 7.4 | 4.4 | — | — | — |
| | | | | 72 | 12[k] | 18.9 | 24.3 | 9.7 | 30.4 | 7.4 | 9.1 | — | 0.4 | 0.01 |
| | | | | | | 33.0 | 35.8 | 11.8 | 6.6 | 7.9 | 4.5 | — | — | — |
| | | | | | FS-7 | 26.4 | 35.7 | 11.5 | | 25.8 | | | | |
| | | | | 78 | 13[m] | 3.6 | 10.1 | 6.7 | 60.6 | 4.9 | 14.0 | — | 0.3 | 0.01 |
| | | | | | | 34.4 | 37.1 | 12.0 | 5.6 | 6.3 | 4.1 | — | 0.1 | — |
| | | | | 85 | →14[n] | 1.7 | 7.5 | 5.8 | 69.6 | 3.8 | 11.2 | — | 0.2 | 0.01 |
| | | | | | | 35.0 | 37.9 | 12.1 | 6.0 | 5.5 | 2.9 | — | — | 0.01 |

[j]Relative sizes of phases, 1:6.1 (t:b)
[k]Relative sizes of phases, 1:14.1 (t:b)
[l]Sample lost during analysis
[m]Relative sizes of phases, 1:8.1 (t:b)
[n]Relative sizes of phases, 1:8.2 (t:b)

COMPARATIVE EXAMPLE A

Following the procedures and using the equipment of Example 3, a sample of unmodified Y-zeolite (CP316-26) was treated with the crude t-butanol/methanol feed mix of Examples 3 and 14, at 200°-220° C. for an extended period. Typical product analyses data are given in Table 15. All product samples were single phase. Summary t-butanol conversion and isobutylene/MTBE selectivities are as follows:

| Sample | Time On Stream (Days) | Operating Temp (°C.) | t-Butanol Conversion (%) |
|---|---|---|---|
| 1 | 3 | 200 | 17 |
| 3 | 14 | 220 | 43 |

TABLE 15

| Ex. | Catalyst | Feed Rate (cc/hr) | Temp. (°C.) | Time On Stream (Days) | Sample | PRODUCT COMPOSITION (WT %) | | | | | | | | |
|---|---|---|---|---|---|---|---|---|---|---|---|---|---|---|
| | | | | | | | | METHOD 26 | | | | METHOD 27 | | |
| | | | | | | $H_2O$ | MeOH | 2-PrOH | $C_4H_8$ | tBA | MTBE | $C_8H_{16}$ | IPTBE | DME |
| 14 | cp316-26[a] | 50 | | | FS-1 | 26.7 | 35.9 | 11.5 | | 25.8 | | | | |
| | | | 200 | 3 | 1 | 24.6 | 37.7 | 11.4 | 2.3 | 21.5 | 2.3 | 0.1 | 0.1 | — |
| | | | | 10 | 2 | 26.4 | 36.1 | 11.4 | 0.7 | 24.5 | 0.7 | — | 0.1 | — |
| | | | 220[b] | 14 | 3 | 25.7 | 36.0 | 11.8 | 5.9 | 14.6 | 5.6 | — | 0.2 | — |

[a]From PQ Corp., 1/16" E
[b]Raise operating temperatures

EXAMPLE 15

Following the procedures and using the equipment of Example 3, a sample of hydrofluoric acid-treated Y-zeolite (CP316-26) prepared by the method of Example 1, was treated with a crude t-butanol/ethanol feed mix at 200° C. Typical product analyses data shown the formation of ethyl t-butyl ether (ETBE) and isobutylene.

I claim:

1. In a method for the etherification of tert-butanol/methanol to methyl tertiary butyl ether over an ion exchange resin etherification catalyst and recovery of the product and bottoms in a primary fractionator, the improvement, allowing more complete conversion of the remaining tertiary butyl alcohol (tBA) fraction in the bottoms to MTBE plus isobutylene, which comprises:
   a) recovering the methyl tertiary butyl ether (MTBE) from the etherification as an overhead fraction in the primary fractionator,
   b) recovering tertiary butyl alcohol, isopropanol and methanol from the etherification as bottoms in the primary fractionator,
   c) removing the bottoms from the primary fractionator, and
   d) reacting said bottoms in a second step over a catalyst comprising an acidic type Y-zeolite having a silica:alumina ratio in the range of 100:1 to 1:1, modified with a fluorine-containing compound selected from the group consisting of hydrogen fluoride, hydrofluoric acid, ammonium fluoride and triflic anhydride, at a temperature from 180° C. to 220° C.

2. The method of claim 1 wherein said Y-zeolite has a Si:Al ratio of 1.5 to 2.

3. The method of claim 1 wherein said Y-zeolite has a silica:alumina ratio of about 8:1.

4. The method of claim 1 wherein said Y-zeolite has a silica:alumina ratio of about 46:1.

5. The method of claim 1 wherein the fluoride-treated Y-zeolite consists essentially of a Y-zeolite having a Si:Al ratio of 1.5-2:1 modified with hydrofluoric acid.

6. The method of claim 1 wherein the fluoride-treated Y-zeolite consists essentially of a Y-zeolite having a silica:alumina ratio of about 46:1 modified with hydrofluoric acid.

7. The method of claim 1 wherein the fluoride-treated Y-zeolite consists essentially of a Y-zeolite having a silica:alumina ratio of about 8:1, modified with ammonium fluoride.

8. The method of claim 1 wherein the modified Y-zeolite catalyst has a residual acidity in the range of 0.1 to 100 mg KOH/gm.

9. The method of claim 1 wherein the hydrogen fluoride or ammonium fluoride are added to the Y-zeolite as aqueous solutions.

* * * * *